(12) United States Patent
Berenguer et al.

(10) Patent No.: US 9,962,080 B2
(45) Date of Patent: May 8, 2018

(54) METHOD FOR ALARM QUALIFICATION AMONG ALARMS STEMMING FROM AN ACTIVITY SUPERVISION SYSTEM

(71) Applicant: ORANGE, Paris (FR)

(72) Inventors: Marc Berenguer, Revel (FR); Marie-Jeanne Bouzid, Echirolles (FR)

(73) Assignee: Orange, Paris (FR)

( * ) Notice: Subject to any disclaimer, the term of this patent is extended or adjusted under 35 U.S.C. 154(b) by 146 days.

(21) Appl. No.: 14/941,387

(22) Filed: Nov. 13, 2015

(65) Prior Publication Data
US 2016/0150957 A1    Jun. 2, 2016

(30) Foreign Application Priority Data
Nov. 28, 2014  (FR) ...................... 14 61649

(51) Int. Cl.
G08B 21/02  (2006.01)
A61B 5/00  (2006.01)
G08B 21/04  (2006.01)

(52) U.S. Cl.
CPC ........ *A61B 5/0002* (2013.01); *G08B 21/0423* (2013.01); *G08B 21/0484* (2013.01)

(58) Field of Classification Search
CPC .............. G08B 21/0219; G08B 21/02; G08B 21/0227; G08B 21/0423; G08B 21/0484; A61B 5/0002; A61B 5/002; A61B 12/006
See application file for complete search history.

(56) References Cited

U.S. PATENT DOCUMENTS 8,249,731 B2 *  8/2012  Tran ...................... A61B 5/1113
                                                        222/23
9,626,858 B2 *  4/2017  Sloo ...................... G08B 29/26
(Continued)

FOREIGN PATENT DOCUMENTS

EP           2472487 A2       7/2012

OTHER PUBLICATIONS

Noury N. et al., "Use of Electrical Devices Reveals Our Well Being", Engineering in Medicine and Biology Society,EMBC, pp. 1769-1772,XP032319078.
(Continued)

*Primary Examiner* — Hai Phan
*Assistant Examiner* — Son M Tang
(74) *Attorney, Agent, or Firm* — Haverstock & Owens LLP (57) ABSTRACT

The invention concerns a method for qualifying an alarm among the alarms stemming from a first supervision system supervising the activity of an individual, the system being adapted to compute an activity index that is representative of the activity of the individual, alarms being triggered by the supervision system in the event of a drift in the activity index, a drift corresponding to a difference in the value of the index in relation to a reference value, the method being such that it is implemented in a management server connected to at least one second supervision system, and that it has, on reception of an alarm triggered by the first supervision system, steps of obtainment of a drift in the activity index of the at least one second supervision system, comparison of the drift in the activity index of the first supervision system and a value that is representative of the drift in the activity index of the at least one second system, and qualification of the alarm according to the result of the comparison. The invention likewise concerns a device and a server imple- (Continued)

menting the method. According to another aspect, the invention concerns a method for requesting alarm qualification and a terminal implementing this method.

11 Claims, 6 Drawing Sheets

(56) References Cited

U.S. PATENT DOCUMENTS

| | | | |
|---|---|---|---|
| 2005/0068165 A1* | 3/2005 | Kelliher | G07C 9/00166 340/523 |
| 2008/0001735 A1 | 1/2008 | Tran | |
| 2009/0135018 A1* | 5/2009 | Veillette | H04L 41/06 340/657 |
| 2013/0257623 A1* | 10/2013 | Bagasra | G08B 27/005 340/657 |
| 2014/0003816 A1* | 1/2014 | Yeh | H04B 10/27 398/66 |
| 2014/0201315 A1* | 7/2014 | Jacob | H04L 12/2803 709/217 |
| 2014/0229128 A1* | 8/2014 | Komano | G01R 21/133 702/61 |
| 2014/0281650 A1* | 9/2014 | Gilbert | H04L 12/2825 713/340 |
| 2015/0097663 A1* | 4/2015 | Sloo | G01N 27/02 340/501 |
| 2015/0100166 A1* | 4/2015 | Baynes | F24F 11/0009 700/278 |
| 2015/0301543 A1* | 10/2015 | Janoso | G05F 1/66 700/291 |
| 2016/0141869 A1* | 5/2016 | Byron | H02J 3/00 700/291 |
| 2016/0173963 A1* | 6/2016 | Filson | H04L 12/1895 340/870.09 |

OTHER PUBLICATIONS

The French Search Report for the FR1461649 Application.

* cited by examiner

METHOD FOR ALARM QUALIFICATION AMONG ALARMS STEMMING FROM AN ACTIVITY SUPERVISION SYSTEM

TECHNICAL FIELD

The present invention relates to the field of medical telemonitoring and particularly concerns a system for assisting in care for elderly, dependent or frail people in the home.

PRIOR ART

The invention is used particularly advantageously for monitoring elderly people living on their own in the home, but can be used for other activity monitoring systems.

The aging of the population in developed countries coupled with a lack of structures for receiving elderly people involves caring for these populations in the home for as long as possible and under optimum conditions.

Nonintrusive systems are known that allow the activity of people living on their own to be monitored in the home. In particular, the publication entitled "*Use of Electrical Devices Reveals Our Well Being*" presented at the annual EMBC conference (Engineering in Medicine and Biology Society, 2011, IEEE, N. Noury, K-A Quach, M. Berenguer, H. Teyssier, M-J Bouzid, L. Goldstein, M. Giordani) describes an activity monitoring system based on the use of domestic electrical appliances. The system uses just a single sensor that is capable of identifying the triggering of the various electrical devices in the home of the monitored person and allows electrical data to be related directly to the activity of the person.

Such systems analyze the activity of people during a first initialization period, in the course of which various indicators are measured and stored in memory. By way of example, the indicators can relate to data relating to the use of electrical appliances, data relating to telephone communications or else to physiological data such as a weighing, for example. The initialization periods may be of different duration according to the indicators under consideration. A statistical analysis of these learning data allows the creation of a reference frame that is specific to a particular situation defined by the characteristics of the environment, the age, sex or past history of the person being supervised.

Following this initialization period, the monitoring system is operational and the indicators under consideration are measured periodically, for example every 24 hours. On the basis of these data, an activity index corresponding to the sum of the differences observed between the indicators of the reference frame and the periodic indicators is established. When a large drift in this activity index is found, an alarm is triggered so as, for example, to draw the attention of the family or of an emergency center to a substantial change in the behavior of the person being monitored. Thus, it is possible to detect a change of nocturnal behavior that a one-off visit would not have been able to reveal, for example.

However, despite all the benefit that such a system has, it has the disadvantage of triggering false alarms in some cases. These false alarms are undesirable because they needlessly mobilize technical and human resources and can be a source of worry for close friends and relatives.

Let us consider, by way of example, the case of a person being monitored who usually goes to bed at around 22:00 hrs. A probe connected to the power grid conveys an indicator relating to the lighting in the residence on a daily basis. This indicator generally makes it possible to establish that the person is indeed in his bedroom at 22:00 hrs. By comparing the indicator with the data stored in memory during the initialization period, the system verifies that the habit is duly observed and does not signal a particular alarm. By contrast, if the person begins to suffer from insomnia and retires much later, the comparison of the indicators with the data stored in memory during the initialization period will allow an alarm to be triggered. However, when this late sleeping is due to an international sporting competition broadcast live on television, for example, triggering of the alarm is inappropriate. Numerous other factors, such as time changes or changes of season, for example, can be the source of false alarms.

One solution can involve resetting the system when significant changes take place, for example at the start of the season, but activity monitoring is then less reliable during the new initialization period. Another solution can involve programming foreseeable events, such as time changes, so that the shift is taken into account during indicator comparison. Nevertheless, some factors such as time changes have a physiological effect on the person that is not foreseeable, and the fact that an external factor is known in advance will not always allow the triggering of an alarm to be avoided.

There is therefore a need for a technical solution that allows the reliability of a home monitoring system to be improved by limiting the rate of false alarms, notably when they are linked to factors that are external to the situation.

SUMMARY OF THE INVENTION

To this end, the invention concerns a method for qualifying an alarm among the alarms stemming from a first supervision system supervising the activity of an individual, the system being adapted to compute an activity index that is representative of the activity of the individual, alarms being triggered by the supervision system in the event of a drift in the activity index, a drift corresponding to a difference in the value of the index in relation to a reference value, the method being such that it is implemented in a management server connected to at least one second supervision system, and that it has, on reception of an alarm triggered by the first supervision system, steps of obtainment of a drift in the activity index of the at least one second supervision system, comparison of the drift in the activity index of the first supervision system and a value that is representative of the drift in the activity index of the at least one second system, and qualification of the alarm according to the result of the comparison.

The drift in the index corresponds to the difference found between the value of this index at a given instant and its value as observed during a reference period. By way of example, an initialization period can be observed following the installation of a supervision system in the home of an individual. The activity is measured during this period using sensors so as to establish an activity index for the individual. The data collected during this initialization period serve as references with which data measured daily using the same sensors are compared so as to detect and quantify any drift.

When a plurality of supervision systems are interconnected, for example by means of a telecommunication network and a management server, the method allows the evolution of an activity index for an individual to be compared with the evolution of an activity index relating to one or more other individuals. By way of example, it is thus possible to determine that a change of behavior at the house of one individual corresponds to the same change at the house of another individual. The reason is that if an external factor such as a time change or a sporting competition causes a change of behavior at the house of a monitored individual, such a change of behavior will probably be found at the houses of other individuals and the situation will be able to be reconsidered as being normal, thus avoiding the triggering of an inappropriate alarm.

In this case, the qualification of an alarm consists in evaluating the relevance thereof and in associating therewith a datum that is representative of this relevance. By way of example, the qualification of an alarm can consist in associating a "confirmed" or "denied" state therewith, or else a degree of relevance on a predetermined scale. A small degree of relevance for an alarm can thus lead to its being cancelled.

According to one particular embodiment, the method is such that the management server is connected to a plurality of second supervision systems and that the comparison step is performed on the basis of the drift in the activity index of the first supervision system and an average for the drift in the activity index of the plurality of second systems.

The drift found by the first supervision system is compared with the average of the drifts found by the other supervision systems connected to the management server. Thus, the method can qualify an alarm more finely, by verifying that the drift found by the first supervision system follows or does not follow the average trend of the other entities.

According to one particular implementation, the method is such that the supervision systems are associated with domestic contexts and that the supervision systems are grouped into classes that are defined by at least one criterion of similarity for the domestic contexts with which they are associated, the comparison step being performed on the basis of the drift in the activity index of the first supervision system and an average for the drift in the activity index of the supervision systems belonging to the same class as the first system.

The domestic context relates to the environment in which the system is installed, such as the configuration of an accommodation, the number of rooms or floors, or else the geographical location of this accommodation. The domestic context can likewise relate to certain characteristics of the individual whose activity is monitored. The method proposes grouping supervision systems into classes according to similarities in the domestic context. By way of example, one class can correspond to elderly people living in an apartment while another corresponds to people in the same age group living in a house. Every kind of criteria relating to the environment and to the physiology of the monitored individual can be used to form classes. In this way, the method allows the drift in the activity index of an individual logged by a supervision system to be compared with an average drift logged by the supervision systems belonging to the same class. The alarms transmitted following a drift in the activity index can thus be qualified much more relevantly.

According to one particular embodiment, the method is such that the activity index drifts are weighted according to a startup date for the corresponding supervision system.

When the supervision system is an expert system that operates by learning, the reliability of the indexes measured increases over time. The weighting of the drifts found on the various systems connected to the management server according to the startup date of the system thus allows preference to be given to the most reliable data during the computation of the average drift in the index.

According to one particular implementation, the method is such that the activity index for a supervision system is established on the basis of a plurality of indicators and in that it additionally has the following steps:
  identification of the preponderant indicator that has caused the drift in the index of the first system,
  obtainment of the drift in the indicator for the at least one second supervision system,
  comparison of the drift in the preponderant indicator of the first supervision system with a value that is representative of the drift in the indicator of the at least one second system, and
  update of the qualification of the alarm according to the result of the comparison.

The activity index is measured on the basis of various indicators. By way of example, these indicators can be established on the basis of movement detectors, electrical activity sensors or a portable device and report on the daily activities of the person being monitored (hygiene, food, television, etc.). The index can be computed so that when one or more indicators drift from their usual value, it causes a drift in the index. The observation of the variations in the index thus makes it possible to find variations in the usual behavior of an individual. However, the single comparison of the drift in such an index that is found for one installation with an average drift in the same index that is found for a set of installations is not always sufficient to confirm a global trend. Thus, the comparison of the drift in the indicator that is primarily responsible for the drift in the index with the average drift in this same indicator in other installations allows or does not allow confirmation of the trend, thus allowing the qualification of the alarm to be updated with better precision. According to one particular implementation, the value that is representative of the drift in the indicator of the at least one second system corresponds to the average of the differences that are found for this indicator in relation to a reference value, the average being able to be computed only for supervision systems in the same class.

According to another particular implementation, the method is such that the at least one criterion of similarity between the domestic contexts has at least one element selected from among the following elements:
  a geographical location,
  the spatial configuration of an environment, and
  a physiological characteristic of the individual.

The various supervision systems connected to the management server are grouped into classes according to the similarity of their domestic context. The domestic context corresponds to the supervised situation and relates to the domestic environment and to physiological characteristics of the person being monitored. By way of example, the domestic context comprises characteristics of the accommodation being supervised and of the individual being monitored. The comparison of the activity index established by a supervision system with the index established by other supervision systems is all the more relevant because the domestic context of the compared systems is similar.

In particular, the method allows supervision systems to be matched according to the geographical location of the installation. By way of example, the geographical location may be a district identifier, a street or else an area of the territory as defined by GPS coordinates. The geographical location criterion can likewise relate to the fact that a supervision system is installed in an urban or rural environment, for example. The method likewise proposes grouping supervision systems according to the spatial configuration of an environment. By way of example, the method can take account of the fact that a supervision system is installed in an accommodation of apartment or house type and can take into consideration the number of rooms in this accommodation as well as the number of floors, for example. The method likewise takes account of the physiological characteristics of an individual being monitored in order to establish groupings between various supervision systems. By way of example, the age of the person being monitored, his weight, his height or else his sex can be taken into account. Taking account of these similarity criteria in order to distribute the supervision systems connected to the management server into classes makes it possible to bring out trends that are particularly relevant with regard to the system under consideration and to distinctly improve the reliability of alarms that can be triggered.

Such an arrangement moreover has the advantage of being able to predict the occurrence of events at the house of an individual when events have already occurred at the houses of individuals having similar domestic contexts. These predictions can be of benefit for insurance companies or personal assistance companies, for example.

According to another aspect, the invention concerns a device for qualifying an alarm among the alarms stemming from a first supervision system supervising the activity of an individual, the system being adapted to compute an activity index that is representative of the activity of the individual, alarms being triggered by the supervision system in the event of a drift in the activity index, a drift corresponding to a difference in the value of the index in relation to a reference value, the device being characterized in that it is connected to at least one second supervision system, and in that it has:

a communication module (504) that is capable of receiving an alarm triggered by the first supervision system,
  a communication module (504) that is capable of obtaining a drift in the activity index of the at least one second supervision system,
  a computer (507) that is capable of computing a value that is representative of the drift in the activity index of the at least one second system,
  a comparator (506) that is capable of comparing the drift in the activity index of the first supervision system with the computed representative value, and
  a qualification module (505) that is capable of qualifying the alarm according to the result of the comparison.

According to yet another aspect, the invention concerns a method for requesting qualification of an alarm on a supervision system supervising the activity of an individual, the system being adapted to compute an activity index that is representative of the activity of the individual, alarms being triggered by the supervision system in the event of a drift in the activity index, a drift corresponding to a difference in the value of the index in relation to a reference value, the method being characterized in that it has the following steps subsequent to the triggering (400) of an alarm:

transmission of an alarm qualification request having a datum relating to the drift in the activity index,
  reception of a message having a qualification for the alarm according to a comparison between the datum relating to the drift in the activity index of the supervision system and a datum relating to the drift in the activity index of at least one second supervision system, and
  transmission of an alarm to an alarm processing server when the alarm is qualified as confirmed.

In this way, a supervision system implementing the method for requesting qualification can consult a server in order to qualify an alarm before requesting an intervention at the home of the person being monitored. The system can thus avoid the triggering of an inappropriate an intervention when a change of behavior is part of a global trend.

The invention also concerns a device for requesting qualification of an alarm on a supervision system supervising the activity of an individual, the system being adapted to compute an activity index that is representative of the activity of the individual, alarms being triggered by the supervision system in the event of a drift in the activity index, a drift corresponding to a difference in the value of the index in relation to a reference value, the device being characterized in that it has a communication module that is implemented on the triggering of an alarm and capable of:

transmitting an alarm qualification request having a datum relating to the drift in the activity index,
  receiving a message having a qualification for the alarm according to a comparison between the datum relating to the drift in the activity index of the supervision system and a datum relating to the drift in the activity index of at least one second supervision system, and
  transmitting the alarm to an alarm processing server when the alarm is qualified as confirmed.

The invention likewise concerns a server comprising a device for qualifying an alarm.

The invention also relates to a terminal comprising a device for requesting qualification of an alarm.

The invention likewise concerns a computer program having the instructions for executing the qualification method and/or the instructions for executing the method for requesting qualification when the program is executed by a processor.

The invention also concerns an information storage medium that can be read by a processor on which is recorded a computer program comprising instructions for executing the steps of the qualification method and/or the steps of the method for requesting qualification.

The various embodiments or implementation features cited above can be added, independently or in combination with one another, to the steps of the qualification method and/or of the method for requesting qualification as defined above.

The servers, terminals, devices, programs and information storage media have at least advantages that are similar to those provided by the compositional method described above.

LIST OF FIGURES

Other features and advantages of the invention will emerge more clearly on reading the description that follows for a particular embodiment, which is provided by way of simple illustrative and nonlimiting example, and the appended drawings, in which.

DETAILED DESCRIPTION

Figure 1:
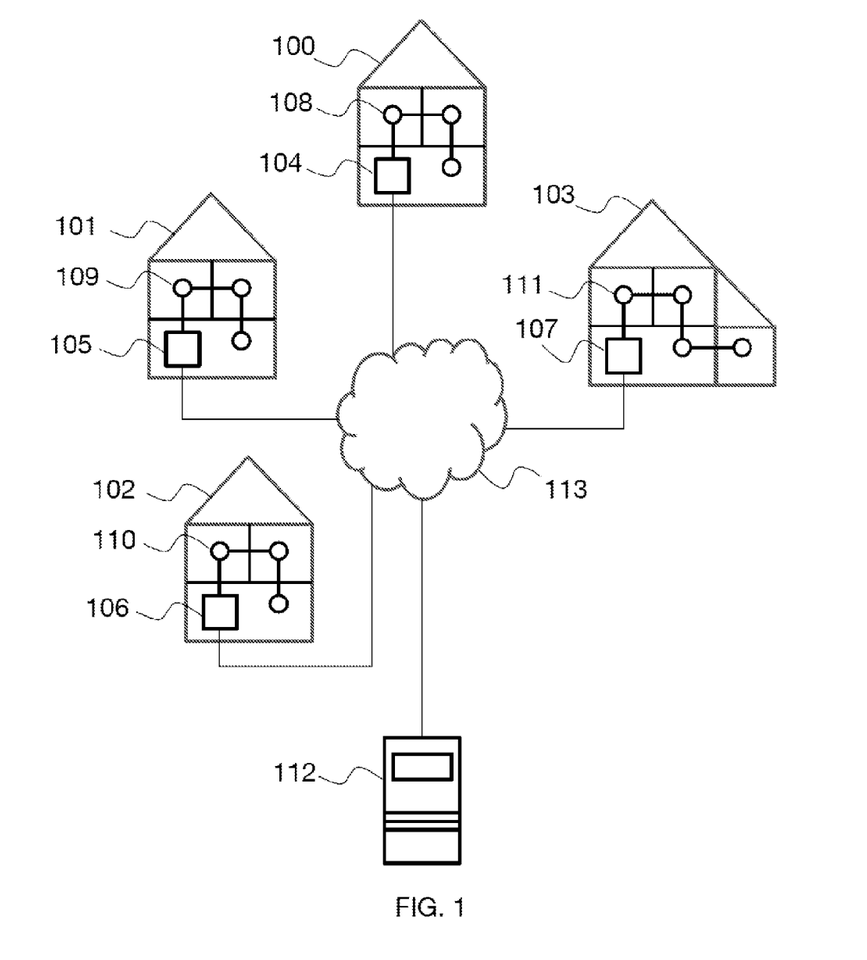
FIG. 1 shows a simplified network architecture that is adapted for implementing the invention according to a particular embodiment.

FIG. 1 shows a simplified network architecture that is adapted for implementing the invention according to a particular embodiment, in which 4 residences 100, 101, 102 and 103 are equipped with a supervision system for monitoring the activity of an inhabitant. These 4 residences are respectively equipped with a control device 104, 105, 106 and 107 and with a network of sensors 108, 109, 110 and 111. The 4 residences are moreover connected to a management server 112 via a communication network 113.

The operation of the supervision system will now be described with reference to the residence 100 in FIG. 1. The systems installed in the other residences in FIG. 1 operate in an identical manner. According to one particular implementation, the supervision system allows the activity of a person in the residence to be monitored. By way of example, this may be a system such as the one described in the document "*Use of Electrical Devices Reveals Our Well Being*" cited in the first part of this presentation. Such a system uses an electrical activity detector connected to the power grid of the residence in order to trace the use of the various electrical appliances in the environment and to deduce the activity of the person therefrom.

On the basis of these use data, the supervision system conveys a certain number of activity indicators for the current life of the person. By way of example, the use of a toaster or a coffee pot by an inhabitant in the mornings allows an indicator relating to the fact that the person takes breakfast at a certain time in the mornings to be conveyed. Still by way of example, detection of the use of appliances such as a hairdryer or a razor allows an indicator relating to the hygiene of the person to be conveyed.

Following the installation of the supervision system in the residence 100, an initialization period is started, during which the activity of the person is stored in memory in a database, for example in a database of the control device 104. The gathered data can likewise be stored in memory on a remote server. During this period, called the reference period, the habits and behaviors of the person being monitored are therefore stored in memory in the form of indicators.

At the end of the initialization period, the indicators are conveyed on a daily basis. The value of each of the indicators is compared with the value of these same indicators as stored in memory during the reference period. Particular attention is paid to the difference in these indicators in relation to the reference value stored in memory during the initialization phase. An index corresponding to the sum of the differences measured for the various indicators is thus computed on a daily basis. This activity index allows changes in the behavior of the person being monitored to be detected. When the index drifts significantly in relation to its reference value computed during the initialization period, and over a certain duration, an alarm is triggered so as to request the intervention of a close friend or relative or a medical team.

Despite the benefit of this solution, changes of behavior can occur without, however, justifying an intervention. As explained earlier on, a time change or a change of season can cause a change of behavior without, however, it being necessary to intervene. Such a system does not provide a satisfactory technical solution for taking into account new conditions justifying a change in the habits of a person being monitored.

Figure 2:
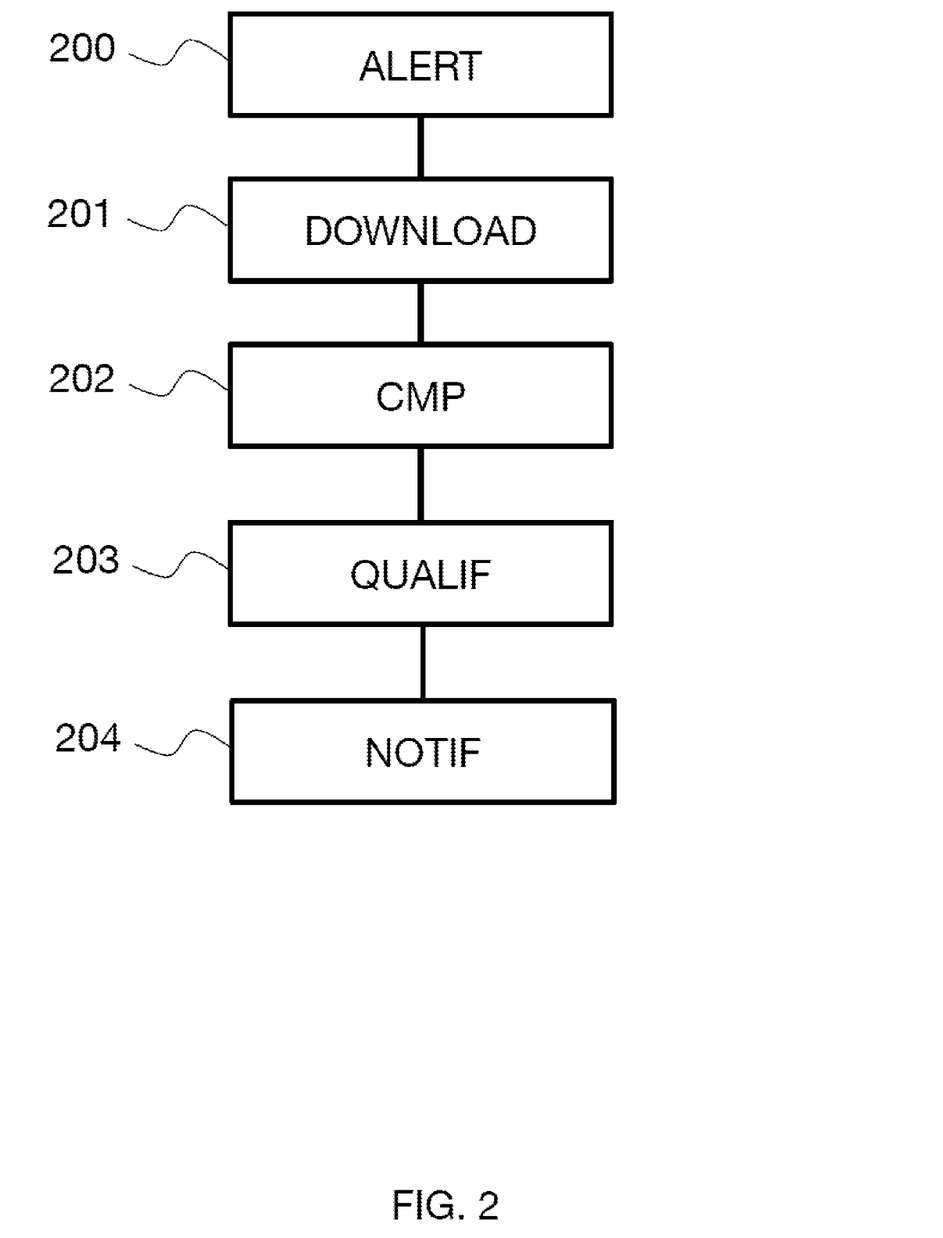
FIG. 2 illustrates the main steps of the qualification method according to one particular implementation.

We will now describe the present invention with joint reference to FIG. 1 and FIG. 2, according to a particular embodiment.

FIG. 2 illustrates the main steps of the method for qualifying an alarm.

The control device 104 in the residence 100 triggers an alarm following observation of a significant drift in the activity index of the person being monitored in step 200. This alarm is intercepted by the server 112 so as to be qualified before triggering an intervention. According to one particular implementation, the control device 104 can transmit an alarm qualification request to the server 112 before actually triggering the alarm.

In a first step 201, the server 112 downloads the daily activity indexes and the reference indexes established during the initialization period by the control devices 104, 105, 106 and 107. According to one particular implementation of the invention, the server 112 downloads the drift in the index rather than the daily index and the reference index. For that purpose, the management server 112 uses the communication network 113, which connects it to the control devices of the residences. So that the server 112 knows the network addresses of the various control devices, the method can involve a prior subscription step, in the course of which the technical information concerning the supervision systems of the 4 residences are communicated to the server. By way of example, the control devices can be preconfigured with the address of the server 112 so that they are able to transmit a recording message on power up, the recording message having a unique identifier for the system and a download address.

In step 202, the management server 112 performs a comparison between the drift in the index logged for the residence 100 at the origin of the alarm and a value that is representative of the drift in the index logged for at least one other of the residences 101, 102 and 103 that are recorded on the server. According to one particular implementation, the value that is representative of the drift in the index that is logged for the residences 101, 102 and 103 is an average for the drift, a standard deviation or any other statistical function allowing a value that is representative of this drift to be obtained.

According to one particular implementation of the invention, the index drifts collected in step 201 are weighted according to the duration of startup of the corresponding supervision systems. By way of example, if the supervision system of the residence 101 has been started up before the system of the residence 102, a higher weight will be assigned to this drift when the average drift is computed. The method thus allows preference to be given to data stemming from supervision systems whose data are rendered more reliable by a longer observation period.

In step 203, the alarm is qualified by the server 112 according to the result of the comparison. By way of example, if the drift logged for the residence 100 corresponds to the average of the drifts found for the other residences recorded on the server 112, the alarm is qualified as a false alarm. If, by contrast, no correlation can be found between the drift in the indexes of the residence 100 and of the residences 101, 102 and 103 then the alarm is confirmed.

In a step 204, the management server transmits a notification to the control device of the residence 100 comprising the qualification of the alarm. On reception of such a request, when the alarm is confirmed, the control device triggers an intervention. By contrast, if the alarm is qualified as a false alarm, the control device does not trigger an intervention.

Thus, the invention allows an advantageous increase in the reliability of the supervision system by avoiding the triggering of an intervention when the change of behavior reflects a global trend among the supervised residences.

Figure 3:
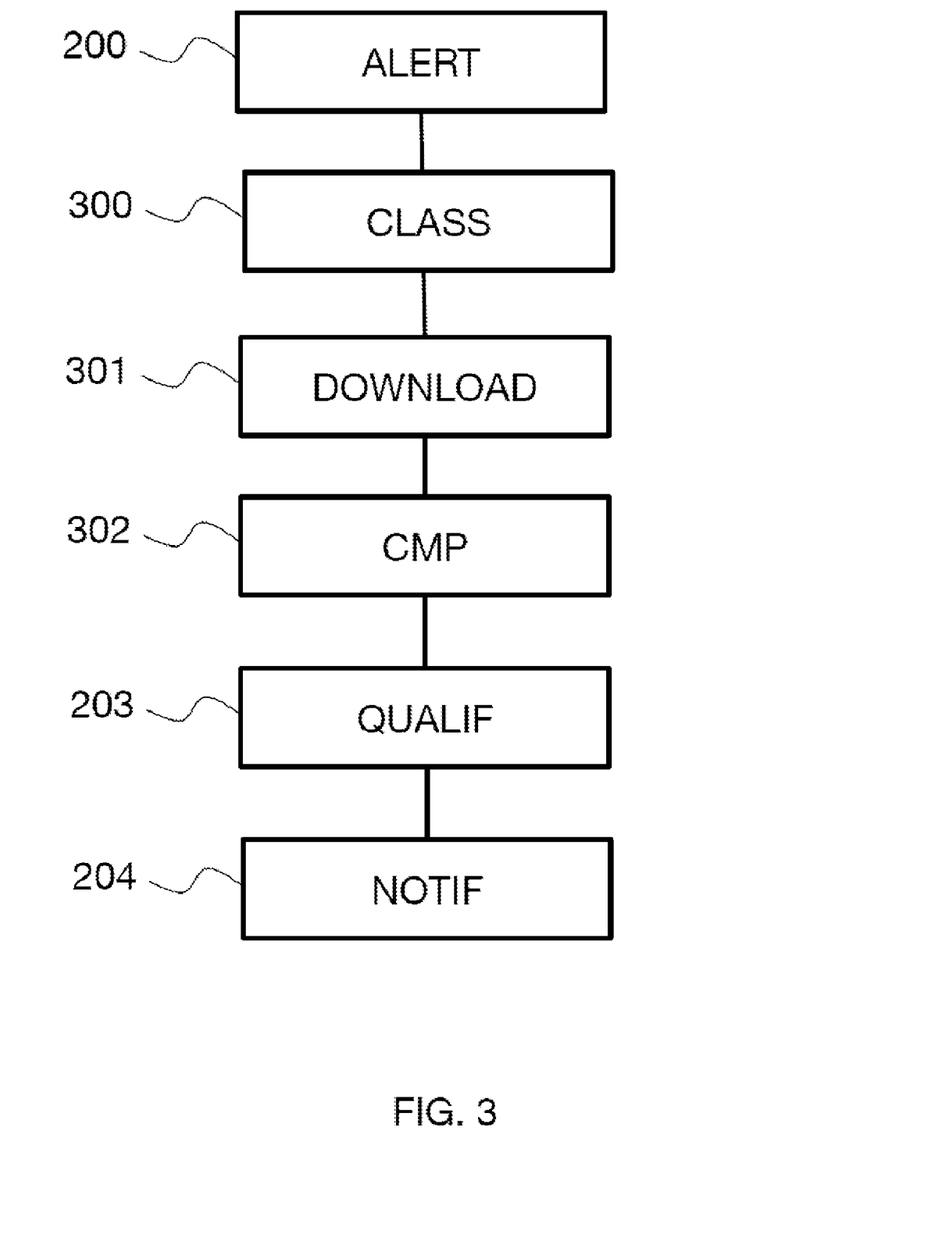
FIG. 3 illustrates the main steps of the qualification method according to another particular implementation.

Another particular embodiment will now be described with reference to FIG. 3.

According to one particular implementation, the information transmitted during a prior recording phase of the various supervision systems comprise, apart from the technical information allowing good communication between the control devices and the management server 112, domestic context information. This information allows the supervised environment to be characterized and comprises, by way of example, the spatial configuration of the accommodation, such as the number of rooms and floors, whether or not it is a single accommodation, the number of bathrooms or whether or not there is a garden. The domestic context can likewise comprise information relating to the geographical location of the accommodation and/or physiological data for the person whose activity is supervised, such as his weight, his height, his sex or his age. These data can be stored in memory in a database of the server 112, for example.

Steps 200, 203 and 204 are identical to those described with reference to FIG. 2.

In a step 300, the server 112 identifies the supervision systems whose domestic context has similarities with the domestic context of the system that has transmitted an alarm qualification request. By way of example, on intercepting an alarm qualification request transmitted for the residence 100, the server 112 consults the domestic context of the supervision system of the residence and compares it with the domestic contexts of the residences 101, 102 and 103 in order to determine a set of residences having a similar context. By way of example the server can compare the number of rooms in the various supervised environments in order to make up a class of supervision systems whose environment is similar. In this example, the server 112 makes up a class having the supervision systems of the residences 101 and 102, the residence 103 being precluded because it has an additional room.

In step 301, only the data relating to the indexes and indexes drifts of the residences 100, 101 and 102 are downloaded.

In step 302, the server 112 performs a comparison between the drift in the index that is found for the residence 100 and the average of the drifts that are found for the supervision systems belonging to the same class as the residence 100. In this example, the activity index of the residences 101 and 102 is used to compute an average for the drifts and to perform a comparison with the drift in the activity index of the residence 100.

The method thus makes it possible to qualify an alarm in a particularly relevant manner by comparing the drift in an activity index associated with a particular supervision system with the average drift of systems supervising similar environments.

According to a particular embodiment, the activity index for a supervision system is established on the basis of a plurality of indicators, and the qualification step 203 moreover has substeps of identification of the preponderant indicator that has caused the drift in the index of the first system, obtainment of the drift in the corresponding indicator for the at least one second supervision system, comparison of the drift in the preponderant indicator of the first supervision system and a value that is representative of the drift in the indicator of the at least one second system, and update of the qualification of the alarm according to the result of the comparison.

For that purpose, the server 112 can, for example using a specific download request, obtain data relating to the drifts in the indicators that have been used to establish the activity index of a supervision system that has requested the qualification of an alarm, so as to determine an indicator whose drift is primarily responsible for the drift in the activity index.

By way of example, following reception, by the server 112, of an alarm qualification request from the control device 104 of the residence 100, said control device can download the various indicators that have been used to compute the activity index. On the basis of these data, the server 112 can determine the indicator that has primarily contributed to the drift in the activity index. By way of example, this may be an indicator whose drift reveals unusual nocturnal activity at the house of the person being monitored. Following the identification of this indicator, the server 112 downloads the drift in this indicator for the other supervised accommodations. According to a particular embodiment, the server can download just the drifts in this indicator for the systems whose domestic context is similar to that of the residence that has triggered the alarm, that is to say the systems of the residences 101 and 102 in this example. The server 112 can then compute a value that is representative of the drift in this indicator for the systems under consideration, such as computing an average for the drifts in the indicator, possibly weighted according to the startup date of the installation, for example. The server 112 can then form a comparison between the drift in the indicator that is observed by the system that has requested qualification of the alarm and the average drift in this indicator for the other systems under consideration before qualifying the alarm according to the result of the comparison.

In this way, the method can advantageously confirm an alarm detected by a supervision system, whereas the comparison alone of the drift in the activity indexes would have led to the alarm being qualified as a false alarm.

Figure 4:
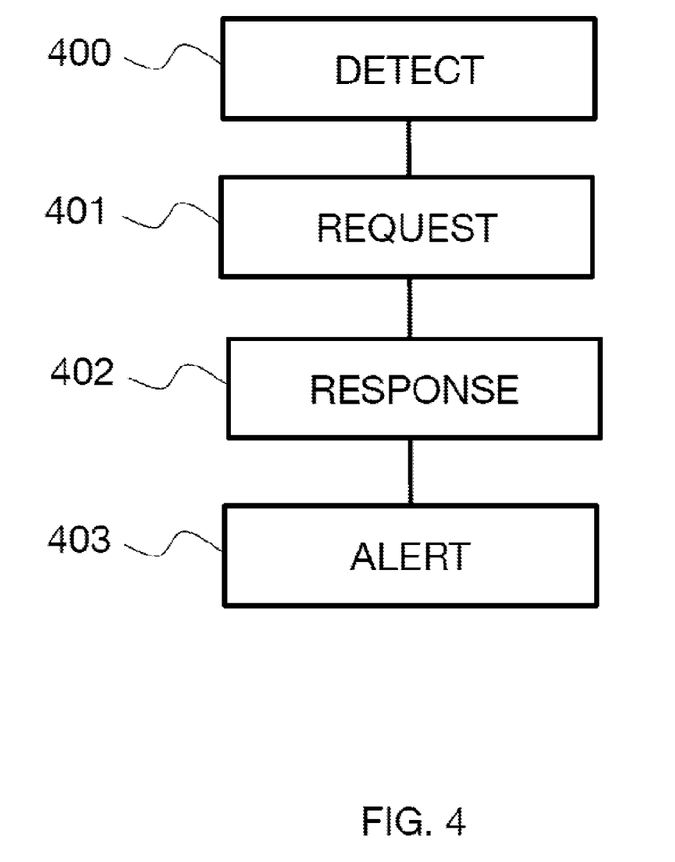
FIG. 4 illustrates the main steps of the download method according to a particular embodiment.

FIG. 4 illustrates the main steps of the method for requesting alarm qualification according to a particular embodiment. In a first step 400, a substantial drift in the activity index is detected by the supervision system. By way of example, the index has deviated from its reference value by 10% in one week. So as not to trigger an inappropriate intervention, the supervision system implements the method for requesting alarm qualification. In step 401, a request is transmitted to a management server, such as the server 112 in FIG. 1, for example. This request particularly has a piece of information relating to the drift in the activity index. By way of example, the request can have the value of the index and the reference value, or else the value of the drift in the index. According to one particular implementation, the request can likewise have a piece of information relating to the drift in the indicator that is primarily responsible for the drift in the index.

The server 112 receives this request in step 200, executes the steps of the method for alarm qualification and transmits a response to the supervision system having the qualification of the alarm.

The supervision system receives the response to the qualification request in a step 402. This response has a piece of information that is dependent on a comparison between the drift in the activity index of the supervision system and a value that is representative of the drift in the activity index of at least one second supervision system, this information allowing the supervision system to know whether or not the alarm is confirmed. When the alarm is confirmed, an alarm is transmitted in step 403 to a server that is capable of triggering an intervention in the home of the person. Otherwise, the drift found is ignored by the supervision system.

Figure 5:
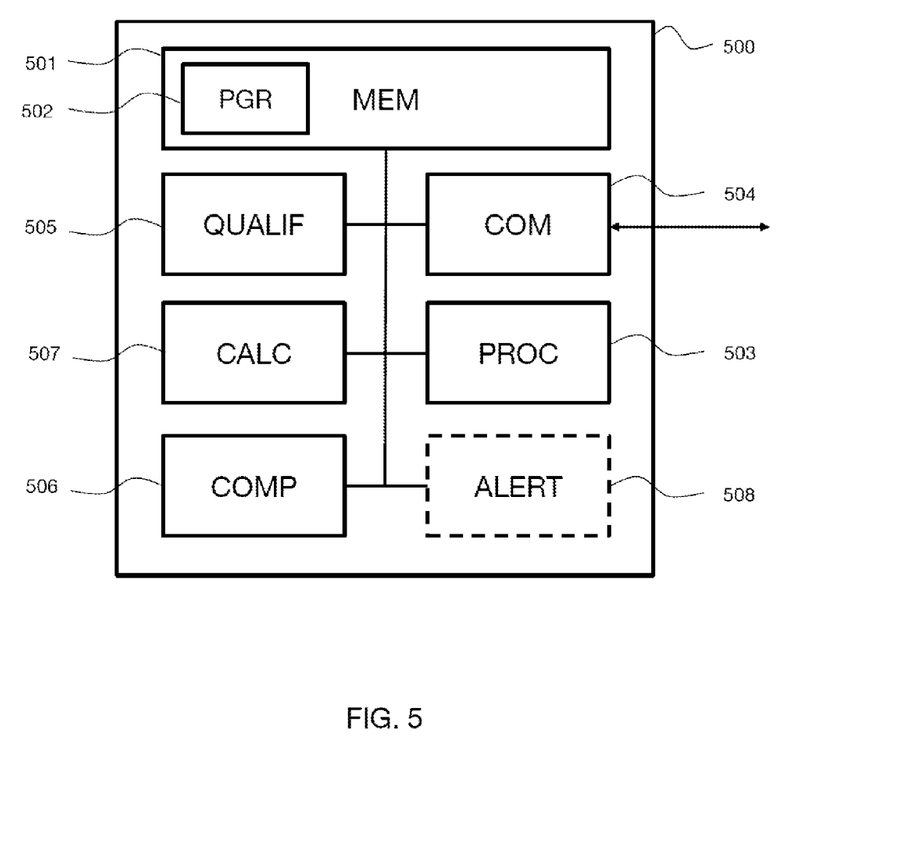
FIG. 5 shows a simplified diagram of a device that is adapted for implementing the method for alarm qualification according to a particular embodiment.

FIG. 5 illustrates a device 500 implementing the qualification method, according to a particular embodiment of the invention. The device comprises a storage space 501, for example a memory MEM, and a processing unit 503, for example equipped with a processor PROC. The processing unit can be driven by a program 502, for example a computer program PGR, implementing the method for alarm qualification as described in the invention with reference to FIGS. 1 to 3, and notably the steps of obtainment of a drift in the activity index of the at least one second supervision system, comparison of the drift in the activity index of the first supervision system and a value that is representative of the drift in the activity index of the at least one second system, and qualification of the alarm according to the result of the comparison.

On initialization, the instructions of the computer program 502 are loaded into a RAM (random access memory in English) memory, for example, before being executed by the processor of the processing unit 503. The processor of the processing unit 503 implements the steps of the compositional method according to the instructions of the computer program 502.

For that purpose, the device comprises, apart from the memory 501, communication means 504 (COM) allowing the device to connect to a telecommunication network and interchange data with other devices by means of the telecommunication network, and, by way of example, to receive an alarm qualification request, to obtain information relating to the drift in an index or in an indicator and to transmit a response message when the alarm is qualified. By way of example, these communication means may be a network interface. The device likewise comprises a computer 507 (CALC) that is capable of computing a value that is representative of the drift in the activity index of the at least one second system. By way of example, the computer 507 can compute an average drift in an index for a set of supervision systems. According to a particular embodiment, the computer 507 can apply a weighting to the various drifts before computing an average therefrom. The device likewise comprises a comparator 506 that is capable of comparing a drift value for an index with an average drift as computed by the unit 507. The device likewise comprises a qualification module, which is adapted for qualifying an alarm on the basis of the result of the comparison performed by the unit 506. Optionally, the device can likewise have an alarm unit 508 that is adapted for requesting an intervention at the supervised home if an alarm is confirmed.

According to a particular embodiment, the device may be integrated in a server.

Figure 6:
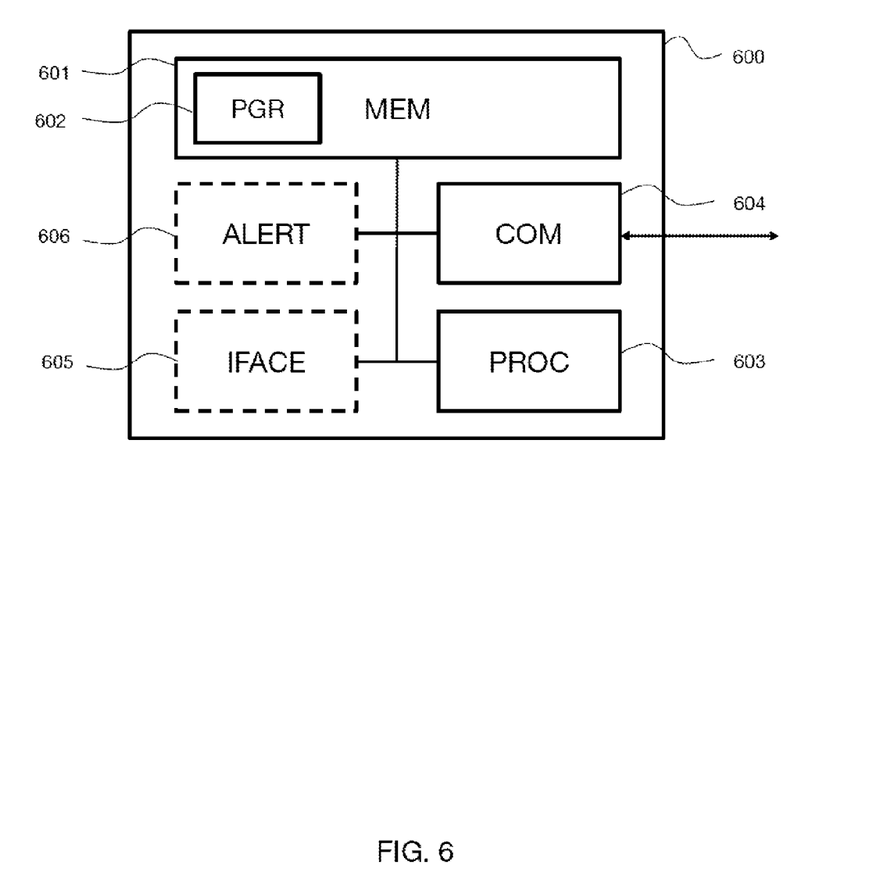
FIG. 6 shows a simplified diagram of a device that is adapted for implementing the method for requesting qualification according to a particular embodiment.

FIG. 6 illustrates a device 600 implementing the qualification request method, according to a particular embodiment of the invention. The device comprises a storage space 601, for example a memory MEM, and a processing unit 603, for example equipped with a processor PROC. The processing unit can be driven by a program 602, for example a computer program PGR, implementing the method for requesting alarm qualification as described in the invention with reference to FIG. 4, and notably the steps of transmission of an alarm qualification request having a datum relating to the drift in the activity index, reception of a message having a qualification for the alarm that is dependent on a comparison between the drift in the activity index of the supervision system and a value that is representative of the drift in the activity index of at least one second supervision system, and transmission of an alarm to an alarm processing server when an alarm is confirmed.

On initialization, the instructions of the computer program 602 are loaded into a RAM (random access memory in English) memory, for example, before being executed by the processor of the processing unit 603. The processor of the processing unit 603 implements the steps of the method for requesting qualification according to the instructions of the computer program 602.

For that purpose, the device comprises, apart from the memory 601, communication means 604 (COM) allowing the device to connect to a telecommunication network and to interchange data with other devices by means of the telecommunication network, and particularly to transmit a request for alarm qualification and to receive a response to this request having the qualification of the alarm.

According to one particular implementation, the device moreover comprises an interfacing unit 605 for interfacing with a supervision system. By way of example, this interfacing unit can correspond to a USB (universal serial bus), Bluetooth or Ethernet interface or else to a communication bus, for example. This interface is adapted for communicating with the supervision system according to a data interchange protocol. According to one particular implementation, the device likewise comprises an alarm unit 606, which is adapted for transmitting a confirmed alarm to an alarm processing server. The alarm unit 606 is adapted for interpreting the message received in response to the qualification request and triggering the alarm when it is confirmed, for example by means of a network interface.

According to a particular embodiment, the device may be integrated in a terminal, a supervision system or else a residential gateway.

The invention claimed is:

1. Method for qualifying an alarm among the alarms stemming from a first supervision system supervising an activity of an individual implemented in a management server connected to the first supervision system and to at least a second supervision system, the system being adapted to compute an activity index that is representative of the activity of the individual, alarms being triggered by the supervision system in an event of a drift in the activity index, a drift corresponding to a difference in the value of the index in relation to a reference value, the method comprising a step of comparing the drift in the activity index of the first supervision system and a value that is representative of the drift in the activity index of the at least one second system, the method being characterized in that the activity index is established on the basis of a plurality of indicators and in that it has, on reception of an alarm triggered by the first supervision system, the following steps:
    identification of a preponderant indicator of the plurality of indicators that has caused the drift in the index of the first system,
    obtainment of the drift in a corresponding indicator corresponding to the preponderant indicator, for the at least one second supervision system,
    comparison of the drift in the preponderant indicator of the first supervision system with a value that is representative of the drift in the corresponding indicator of the at least one second system, and
    qualification of the alarm according to the result of the comparison, the alarm being confirmed if the drift in the preponderant indicator of the first supervision system is not correlated with the value that is representative of the drift in the corresponding indicator of the at least one second system.

2. Method according to claim 1, characterized in that the management server is connected to a plurality of second supervision systems and in that the comparison step is performed on the basis of the drift in the activity index of the first supervision system and an average for the drift in the activity index of the plurality of second systems.

3. Method according to claim 1, characterized in that the supervision systems are associated with domestic contexts and in that the supervision systems are grouped into classes that are defined by at least a spatial configuration of the domestic contexts with which they are associated, the comparison step being performed on the basis of the drift in the activity index of the first supervision system and an average for the drift in the activity index of the supervision systems belonging to the same class as the first system.

4. Method according to claim 1, characterized in that the activity index drifts are weighted according to a startup date for the corresponding supervision system.

5. Device for qualifying an alarm among the alarms stemming from a first supervision system supervising an activity of an individual, the system being adapted to compute an activity index that is representative of the activity of the individual, alarms being triggered by the supervision system in the event of a drift in the activity index, a drift corresponding to a difference in the value of the index in relation to a reference value, the device being characterized in that it is connected to at least one second supervision system, and in that the activity index is established on the basis of a plurality of indicators and in that it has:
    a communication module that is capable of receiving an alarm triggered by the first supervision system,
    the communication module is further capable of obtaining a drift in the activity index of the at least one second supervision system,
    a computer that is capable of computing a value that is representative of the drift in the activity index of the at least one second system,
    a comparator that is capable of comparing the drift in a preponderant indicator of the plurality of indicators of the first supervision system with a value that is representative of the drift in a corresponding indicator of the at least one second system, and
    a qualification module that is capable of qualifying the alarm according to the result of the comparison.

6. Method for requesting qualification of an alarm on a supervision system supervising the activity of an individual, the system being adapted to compute an activity index that is representative of the activity of the individual, alarms being triggered by the supervision system in an event of a drift in the activity index, a drift corresponding to a difference in a value of the index in relation to a reference value, the method being characterized in that it has the following steps subsequent to the triggering of an alarm:
    transmission of an alarm qualification request having a datum relating to the drift in the activity index,
    reception of a message having a qualification for the alarm according to a comparison between the datum relating to the drift in the activity index of the supervision system and a datum relating to the drift in the activity index of at least one second supervision system, wherein the activity index is established on the basis of a plurality of indicators and the drift in a preponderant indicator of the plurality of indicators of the supervision system is compared with a value that is representative of the drift in a corresponding indicator of the at least one second supervision system, and
    transmission of the alarm to an alarm processing server when the alarm is qualified as confirmed.

7. Device for requesting qualification of an alarm on a supervision system supervising the activity of an individual, the system being adapted to compute an activity index that is representative of the activity of the individual, alarms being triggered by the supervision system in an event of a drift in the activity index, a drift corresponding to a difference in a value of the index in relation to a reference value, the device being characterized in that it has a communication module that is implemented on the triggering of the alarm and capable of:
    transmitting the alarm qualification request having a datum relating to the drift in the activity index,
    receiving a message having a qualification for the alarm according to a comparison between the datum relating to the drift in the activity index of the supervision system and a datum relating to the drift in the activity index of at least one second supervision system, wherein the activity index is established on the basis of a plurality of indicators and the drift in a preponderant indicator of the plurality of indicators of the supervision system is compared with a value that is representative of the drift in a corresponding indicator of the at least one second supervision system, and
    transmitting the alarm to an alarm processing server when the alarm is qualified as confirmed.

8. Management server characterized in that it has a device for qualifying an alarm among the alarms stemming from a first supervision system supervising an activity of an individual, the system being adapted to compute an activity index that is representative of the activity of the individual, alarms being triggered by the supervision system in an event of a drift in the activity index, a drift corresponding to a difference in a value of the index in relation to a reference value, the device being characterized in that it is connected to at least one second supervision system, and in that the activity index is established on the basis of a plurality of indicators and in that it has:
    a communication module that is capable of receiving an alarm triggered by the first supervision system,
    the communication module is further capable of obtaining a drift in the activity index of the at least one second supervision system,
    a computer that is capable of computing a value that is representative of the drift in the activity index of the at least one second system,
    a comparator that is capable of comparing the drift in a preponderant indicator of the plurality of indicators of the first supervision system with a value that is representative of the drift in a corresponding indicator of the at least one second system, and
    a qualification module that is capable of qualifying the alarm according to the result of the comparison.

9. Terminal characterized in that it has a device for requesting alarm qualification for requesting qualification of an alarm on a supervision system supervising an activity of an individual, the system being adapted to compute an activity index that is representative of the activity of the individual, alarms being triggered by the supervision system in an event of a drift in the activity index, a drift corresponding to a difference in a value of the index in relation to a reference value, the device being characterized in that it has a communication module that is implemented on the triggering of an alarm and capable of:

transmitting the alarm qualification request having a datum relating to the drift in the activity index, receiving a message having a qualification for the alarm according to a comparison between the datum relating to the drift in the activity index of the supervision system and a datum relating to the drift in the activity index of at least one second supervision system, wherein the activity index is established on the basis of a plurality of indicators and the drift in a preponderant indicator of the plurality of indicators of the supervision system is compared with a value that is representative of the drift in a corresponding indicator of the at least one second supervision system, and transmitting the alarm to an alarm processing server when the alarm is qualified as confirmed.

10. Non-transitory information storage medium that can be read by a processor on which is recorded a computer program comprising instructions for executing steps of a method for qualifying an alarm among the alarms stemming from a first supervision system supervising an activity of an individual, the system being adapted to compute an activity index that is representative of the activity of the individual, wherein the activity index is established on the basis of a plurality of indicators, the alarm being triggered by the supervision system in an event of a drift in the activity index, a drift corresponding to a difference in a value of the index in relation to a reference value, the method being characterized in that it is implemented in a management server connected to at least one second supervision system, and in that it has, on reception of the alarm triggered by the first supervision system, the following steps:

identification of a preponderant indicator of the plurality of indicators that has caused the drift in the index of the first system, obtainment of the drift in a corresponding indicator corresponding to the preponderant indicator, for the at least one second supervision system, comparison of the drift in the preponderant indicator of the first supervision system with a value that is representative of the drift in the corresponding indicator of the at least one second system, and qualification of the alarm according to the result of the comparison.

11. Non-transitory information storage medium that can be read by a processor on which is recorded a computer program comprising instructions for executing steps of a method for requesting qualification of an alarm on a supervision system supervising an activity of an individual, the system being adapted to compute an activity index that is representative of the activity of the individual, alarms being triggered by the supervision system in an event of a drift in the activity index, a drift corresponding to a difference in a value of the index in relation to a reference value, the method being characterized in that it has the following steps subsequent to the triggering of an alarm:

transmission of the alarm qualification request having a datum relating to the drift in the activity index, reception of a message having a qualification for the alarm according to a comparison between the datum relating to the drift in the activity index of the supervision system and a datum relating to the drift in the activity index of at least one second supervision system, wherein the activity index is established on the basis of a plurality of indicators and the drift in a preponderant indicator of the plurality of indicators of the supervision system is compared with a value that is representative of the drift in a corresponding indicator of the at least one second supervision system, and transmission of the alarm to an alarm processing server when the alarm is qualified as confirmed.

\* \* \* \* \*